United States Patent [19]

Gueret

[11] Patent Number: 5,890,828
[45] Date of Patent: Apr. 6, 1999

[54] PACKAGING AND APPLICATION UNIT

[75] Inventor: Jean-Louis H. Gueret, Paris, France

[73] Assignee: L'Oreal, Paris, France

[21] Appl. No.: 950,596

[22] Filed: Oct. 15, 1997

[30] Foreign Application Priority Data

Oct. 15, 1996 [FR] France ................................. 96-12565

[51] Int. Cl.⁶ ............................. A45D 34/00; A45D 40/20
[52] U.S. Cl. ........................ 401/126; 401/119; 401/123; 401/127; 401/130
[58] Field of Search .................................. 401/119, 126, 401/130, 127, 123

[56] References Cited

U.S. PATENT DOCUMENTS

| 5,492,426 | 2/1996 | Gueret | 401/126 |
| 5,636,931 | 6/1997 | Gueret | 401/126 |

FOREIGN PATENT DOCUMENTS

| 0 380 182 | 8/1990 | European Pat. Off. . |
| 0 612 488 A1 | 8/1994 | European Pat. Off. . |
| 0 667 301 A1 | 8/1995 | European Pat. Off. . |
| 0 688 516 A1 | 12/1995 | European Pat. Off. . |
| 2 290 863 | 6/1976 | France . |
| 44 34 793 A1 | 4/1996 | Germany . |

Primary Examiner—David J. Walczak
Assistant Examiner—Tuan N. Nguyen
Attorney, Agent, or Firm—Oblon, Spivak, McClelland, Maier & Neustadt, P.C.

[57] ABSTRACT

A packaging and application unit, including an applicator containing a product capable of becoming soluble or gelling on its surface in contact with a liquid composition, and a reservoir containing the liquid composition. In use, the applicator is placed into contact with the liquid composition through an elastically deformable element which is capable of containing a quantity of the liquid composition, and is capable of selectively passing from a compressed position wherein at least a portion of the surface of the applicator bears on a restoring surface of the deformable element, so as to be in contact with the liquid composition, into a rest position. Passing from the compressed position to the rest position produces the charging of the deformable element with the liquid composition by suction through a charging surface of the deformable element.

20 Claims, 3 Drawing Sheets

PACKAGING AND APPLICATION UNIT

BACKGROUND OF THE INVENTION

1. Field of the Invention

The present invention concerns a packaging and application unit capable of being used, in particular, in the fields of pharmacy, cosmetics, dermatology, hair care and etc. The invention concerns more particularly a device of the type comprising a solid or semi-solid applicator which must be placed into contact with a liquid composition before the application, and capable of becoming soluble or of gelling at its surface which contacted the liquid composition. By way of example, the applied material of the applicator may be a slightly friable lipstick whose surface must be placed into contact with water for example, in order to soften it on its surface, and thus to promote the friability of the lipstick. Again, by way of example, the applicator may be of the "styptic pencil" type used for cauterizing wounds. In the previous example, the applicator contains active water-soluble substances such as mixtures of aluminum and ammonium sulphates which become soluble in the presence of a liquid composition such as water. The invention also applies to the application of a product capable of having both a cosmetic effect and a treatment effect. The cosmetic effect being produced by the applicator itself, and the treatment effect being obtained by a liquid solution with which the applicator is placed into contact. By way of example, this concerns a lipstick that is placed into contact with a treatment composition which prevents the cracking of lips. It may also be a stearate soap of ammonium or potassium, or a tensioning stick, for example, of polyvinyl alcohol (PVA) capable of erasing wrinkles. It may also be a compound such as an emollient which may not be introduced into the stick during its manufacture.

2. Discussion of the Background

European Patent 612 488 describes an applicator comprising a reservoir containing a product to be applied, a cap intended to close the reservoir and an applicator holder supporting a deformable element, for applying the product, made of foam or an elastomer of low hardness. The deformable element has asperities on its surface and is provided with the ability to regain its original shape.

The reservoir for the product is delimited by a capillary end fitting in the shape of a glove finger having a bottom provided with a seat pierced by at least one capillary opening against which the deformable element is applied and deformed in its position when the reservoir is closed by the cap.

SUMMARY OF THE INVENTION

One object of the invention is to create a packaging and application device, whereof at least a portion of the surface of the applicator is kept in contact with a liquid composition.

According to the invention, a packaging and application unit is made having a longitudinal axis. The packaging and application unit includes an applicator in the form of an element containing a product capable of becoming soluble or gelling on its surface when put in contact with a liquid composition, a reservoir containing the liquid composition with which the applicator has to be placed into contact with before the application, and an elastically deformable element. In practice, the applicator is placed in contact with the liquid composition by way of the elastically deformable element which is capable of containing a quantity of the liquid composition. The elastically deformable element is capable of selectively passing from (i) a compressed condition, wherein at least a portion of the surface of the applicator bears, along the direction of the longitudinal axis, on a restoring surface of the elastically deformable element so as to be in contact with the liquid composition, into (ii) a rest position. Wherein the passing from the compressed position to the rest position produces the charging of the deformable element with the liquid composition by suction through a charging surface of the deformable element.

Advantageously, the elastically deformable element is made of foam or an elastomer of low hardness and is carried by the reservoir. Furthermore, a cap is provided which is mounted in a detachable manner on the reservoir and which carries an applicator holder whereon the applicator is mounted. The applicator bears on the restoring surface of the elastically deformable element so as to compress the elastically deformable element along the longitudinal axis while keeping the applicator in contact with the liquid composition when the cap is in the closed position. When the cap is opened and withdrawn, the withdrawal of the applicator produces the charging of the elastically deformable element through the charging surface by a pumping effect. The reservoir may be a tube. The reservoir may be made, at least partly, of a translucent material to allow the quantity of liquid remaining in the reservoir to be seen.

The arrangement of the elastically deformable element in accordance with the invention makes it possible to obtain several functions in a simple manner. When the elastically deformable element is compressed on a seat of the reservoir, the elastically deformable element ensures the sealing of the reservoir. The shape memory of the elastically deformable element permits the function of pumping and drawing the product during the opening and withdrawal of the applicator, subsequently allowing the applicator to contact the liquid composition when the cap is in the closed position. Moreover, it makes it possible to compensate for any clearance due to use and hence removal of the product of the applicator (in the case of a lipstick for example). The elastically deformable element may have an abrasive function to promote the friability of the applicator in water, for example.

The elastically deformable element can be mounted inside a glove finger-type element having a bottom with which the charging surface of the elastically deformable element is placed into contact. The bottom of the glove finger having means capable of retaining a quantity of the liquid composition by the surface tension or capillarity effect. Such means may include at least one opening and/or at least one slot arranged in the bottom of the glove finger.

Advantageously, the bottom of the glove finger has a plurality of slots forming concentric portions of circular arcs. In an alternative, the bottom of the glove finger has a plurality of radial slots. Such slots and/or openings may open out in the reservoir along a frustoconical flared portion and perform a reservoir function by the surface tension effect or by the effect of capillarity.

According to a particular embodiment, the bottom of the glove finger has a central opening capable of being selectively obturated by a valve whose opening is produced by the compression of the elastically deformable element; the opening of the cap and the withdrawal of the applicator producing the closing of the valve. Alternatively, the opening of the valve may be produced by the opening of the cap and the withdrawal of the applicator; the closing is produced by the compression of the elastically deformable element.

The applicator may take the form of a stick of a solid or semi-solid product, friable on its surface when put in contact with a liquid composition. The applicator being mounted on the applicator holder by means of a mechanism forming a spring so as to compensate for the shortening of the applicator in the course of use. Alternatively, the shortening of the applicator can be compensated by raising the elastically deformable element at the bottom of the glove finger by means of a mechanism forming a spring.

The elastically deformable element may be mounted at the bottom of the glove finger by bonding, welding, riveting or by catch engagement by means of an annular collar.

The restoring surface of the elastically deformable element may be covered by a flocked coating, a perforated film of a thermoplastic elastomer, a plastic, a layer of felt or a layer of textile material. This characteristic makes it possible, inter alia, to adjust the quantity of liquid transferred onto the applicator.

According to the invention, the applicator may be a styptic pencil, a lipstick, a stick of polyvinyl alcohol (PVA), a stick of guar gum or a stick of a product for the treatment of the skin. By way of example, the liquid composition contains water or any other solvent and/or preservatives and/or emollients and/or active compounds, the liquid composition having to be capable of being drawn in by the elastically deformable element.

BRIEF DESCRIPTION OF THE DRAWINGS

To render the present invention more readily understood, some preferred embodiments will be described below by way of purely illustrative and nonrestrictive examples, represented in the attached drawings, wherein.

DESCRIPTION OF THE PREFERRED EMBODIMENTS

Figure 1:
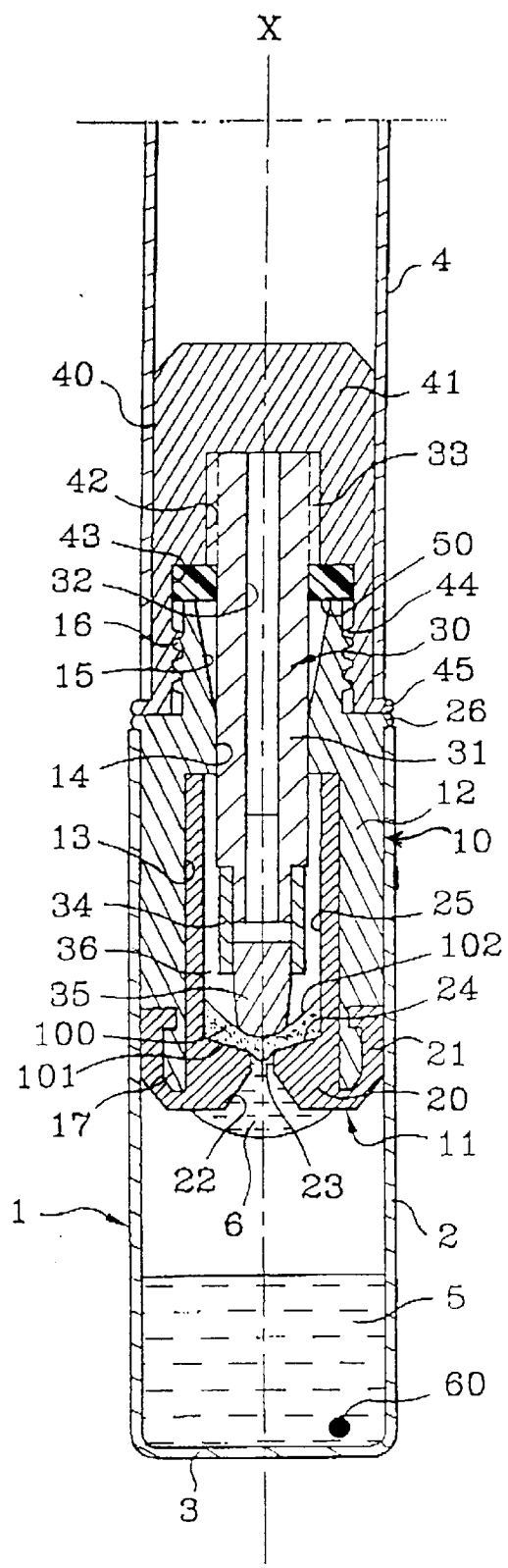
FIG. 1 is a partial sectional view of an application unit in accordance with the invention.

Referring now to the drawings, wherein like reference numerals designate identical or corresponding parts throughout the several views, and more particularly to FIG. 1 thereof, the application unit comprises a reservoir 2 of a cylindrical shape, having a bottom 3 and being open at one end. A distance sleeve 10 of a slightly smaller diameter than the internal diameter of the reservoir 2 is force-fitted through this open end until a stop of the collar 26 of the distance sleeve 10, having an external diameter substantially equal to the external diameter of the reservoir 2, comes to bear against the front external edge of the opening of the reservoir 2.

The distance sleeve 10 carries a thimble-shaped end fitting 11. For this purpose, the distance sleeve 10 has an axial cylindrical recess 13 extended along a smaller diameter coaxial passage 14, itself extended along an outwardly divergent flared portion 15. Opposite this flared portion 15, the distance sleeve 10 carries an external thread 16 on the surface of a cylindrical end portion having a diameter smaller than that of the portion of the distance sleeve 10 fitted in the reservoir 2.

At the end of the distance sleeve 10 remote from that carrying the thread 16, the distance sleeve 10 is provided with an annular catch engagement bulge 17. The end fitting 11 is accommodated in the cylindrical recess 13. The end fitting 11 has the shape of a thimble, defining a cylindrical chamber 25 and a bottom 20. The bottom 20 has a seat 24 pierced by a capillary opening 23 capable of retaining, by means of the surface tension effect, a certain quantity of the product or liquid composition 5 in the form of a drop 6. The bottom 20 is surrounded by a catch engagement collar 21 of a shape complementary to that of the annular bulge 17 of the distance sleeve 10, thus making it possible to join the end fitting 11 to the distance sleeve 10 by catch engagement. The bottom 20 of the end fitting 11 is interspaced from the bottom 3 of the reservoir 2 containing the liquid composition 5 to be placed into contact with the applicator.

Figure 2:
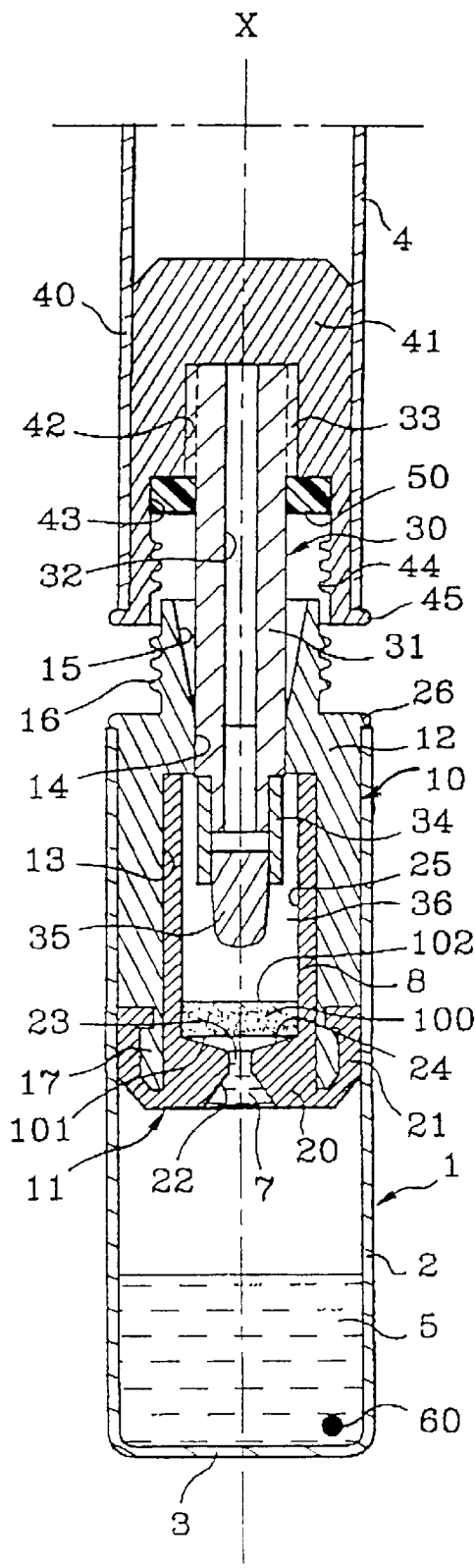
FIG. 2 is similar to FIG. 1, but the application unit is shown in an open position.

The application unit also comprises a cap 4 only a part of which is shown in FIGS. 1 and 2. The cap 4 also has the shape of a cylinder closed at one of its ends, and open at the other end. A stopper 40, of the same cross-section as the cap 4 which itself has a cross-section similar to that of the reservoir 2, is force-fitted through this opening. The stopper 40 is fitted in the cap 4 until a collar 45 of the stopper 40 comes to bear against the external edge of the opening of the cap 4. The stopper 40 has a cap portion 41 in which is arranged a cavity 42 which is extended in a larger diameter bore 43 internally carrying a thread 44 complementary to the thread 16 carried by the distance sleeve 10.

The stopper 40 is joined to an applicator holder 30 supporting an applicator element 35 (represented in the form of a stick, for example, a lipstick). Typically, such an applicator element 35 comprises a product packaged in the form of a solid or semi-solid stick. The product is capable of becoming soluble or of gelling on its surface when put in contact with an appropriate liquid composition, with a view to its becoming friable, on the skin for example. Preferably, the product of the applicator element 35 is not friable, or is friable only to a small extent in its dry state, but becomes friable on its surface when it is placed into contact with a liquid composition. Preferably, the product of the applicator element 35 does not absorb or draw the liquid in depth, so that the solubilization or gelling is produced solely on its surface. Such a stick can be obtained by molding or by extrusion. The applicator holder 30 comprises a hollow stem 31 pierced by a bore 32, and at one end it has longitudinal fins 33 for holding the stem 31 in position in the cavity 42 of the cap portion 41 by a force fit. The other end of the stem 31 is provided with a rigid holding sleeve 34 in the form of an open glove finger, wherein the applicator element 35 is fitted by force. In a variant, not shown, the applicator element 35 is carried directly by the hollow stem 31.

According to the invention, an elastically deformable element 100 is disposed in the bottom 20 of the end fitting 11. This elastically deformable element 100 is advantageously constituted by a block of foam with open, or half open cells, or by a block of an elastomer of low hardness, wherein the open or half open cells communicate with one another when the elastically deformable element 100 has not been substantially deformed. The term "elastomer of low hardness" is understood to refer to an elastomer whose hardness is from 15 Shore A to 70 Shore A. This elastomer is also formed as a foam with open or half open cells. One side or charging surface 101 of the elastically deformable element 100 faces both the bottom 20 of the end fitting 11 and the opening 23 capable of retaining a quantity of the liquid composition 5 by the surface tension effect. The other side or restoring surface 102 of the elastically deformable element 100 faces the applicator element 35. The applicator element 35 is mounted in such a way that, in the closed position of the cap 4, the application end of the applicator element 35 bears on the restoring surface 102 of the elastically deformable element 100 so as to compress it along the X-axis of the application unit against both the seat 24 of the bottom 20 of the end fitting 11 and the opening 23. Thus when the elastically deformable element 100 is charged with the liquid 5, the applicator element 35 is in contact with the liquid 5 in this closed position. In this closed position, illustrated in FIG. 1, the cap 4 is screwed onto the reservoir 2, a sealing gasket 50 being placed round the stem 31 between the stopper 40 and the distance sleeve 10. Yet other arrangements may be used in a conventional manner to ensure the seal of the packaging unit.

FIG. 2 shows the application unit in an open position just before use. In this position, the applicator element 35 no longer bears on the elastically deformable element 100. The end of the applicator element 35 that was in contact with the liquid 5 is rendered soluble or gelled on its surface. The product of the applicator element 35 can then be broken down, on the skin for example. The elastically deformable element 100 has reassumed its initial shape while drawing in at least a proportion of the drop 6 of the liquid product 5, the remainder 7 of the liquid product 5 obstructing the opening 23 wherein it is held in position by the surface tension effect. Thus after use, by screwing down the cap 4, the applicator element 35 is again placed into contact with the restoring surface 102 of the elastically deformable element 100 which is impregnated with the liquid product 5. In fact, it should be noted that in accordance with the invention, the transfer of the liquid product 5 to the applicator element 35 is effected when the applicator element 35 is caused to bear on the elastically deformable element 100, but also simultaneously with the withdrawal of the applicator element 35, as long as the applicator element 35 is still in contact with the foam material of the elastically deformable element 100. Indeed, as will be seen in greater detail below, a valve may be provided whose opening is actuated by the elastically deformable element 100 passing into its rest position, that is to say, during its decompression.

Advantageously, the absorption capacity of the elastically deformable element 100 is greater than the quantity of the liquid transferred to the applicator element 35, so that it is possible to impregnate or remoisten the applicator element 35 without having to screw down the cap 4 again onto the reservoir 2. For this purpose, a sufficient thickness of foam material of the elastically deformable element 100 is provided to allow the desired drawing in, and slots or openings are provided in sufficient numbers and size, to retain a sufficient quantity of liquid product 5 by the surface tension or capillarity effect.

A ball 60 is accommodated in the reservoir 2 and allows the liquid product 5 to be shaken, if necessary. The opening 23 opens out in the reservoir 2 along a flared frustoconical portion 22. Due to this opening 23, whose diameter may be of the order of 0.5 mm to 3 mm, a drop 6 of the liquid product 5 is attached to the bottom 20 of the end fitting 11 by the surface tension effect or capillarity.

Yet other arrangements may be used for charging the elastically deformable element 100 with liquid. By way of example, there may be mentioned an element in the form of a mesh, for example, of felt, of which one end is in contact with the liquid product 5 composition.

The elastically deformable element 100 may be mounted on the bottom 20 of the end fitting 11 by any appropriate means. By way of example, it may be mounted by bonding, welding or riveting or by catch engagement by means of an annular collar.

Figure 3:
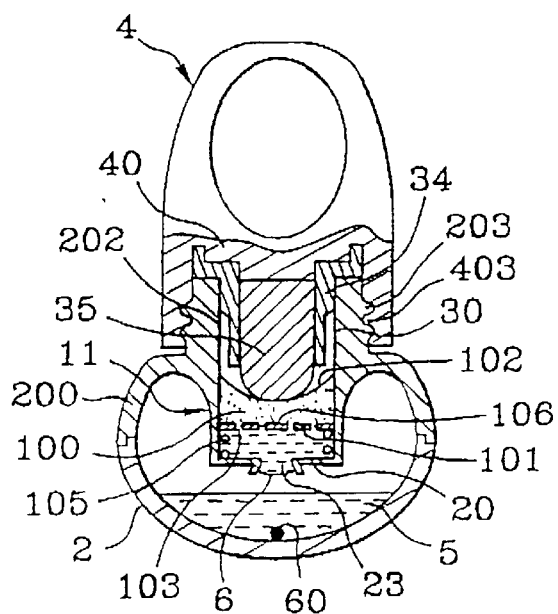
FIG. 3 is a partial sectional view of a variant of the application unit in accordance with the invention.
Figure 4:
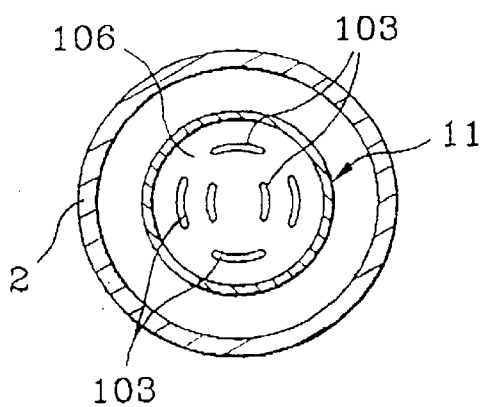
FIG. 4 shows a sectional view of a special arrangement of the element whereon the elastically deformable element is mounted.
Figure 6:
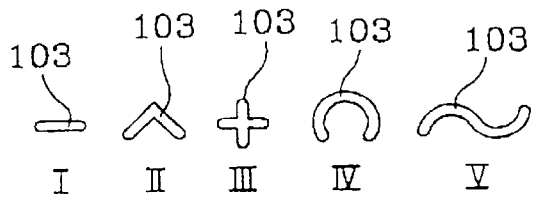
FIGS. 6/I to 6/V show various cross-sectional shapes for the opening for retaining the liquid by the surface tension effect.
Figures 7, 8:
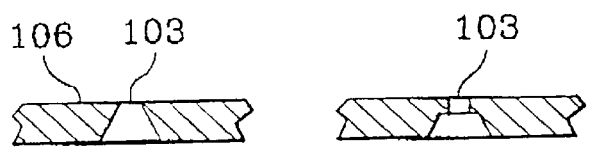
FIGS. 7 and 8 show longitudinal sections of two variants of the opening for retaining the liquid by the surface tension effect.

FIG. 3 shows a variant of the application unit, wherein the elastically deformable element 100 is mounted at the bottom 20 of the end fitting 11 by means of a plate 106 mounted on a spring 105. When the applicator element 35 is withdrawn, the plate 106 rises up again under the effect of the restoring force of the spring mechanism 105 while producing a piston effect, so as to promote the rising of the liquid product 5 in the elastically deformable element 100 through the openings or slots 103 arranged in the plate 106, as will be seen in greater detail below. For the purpose of illustration and clarity, the space between the bottom 20 and the plate 106 has been exaggerated. The bottom 20 of the end fitting 11 itself is pierced by an opening 23 allowing the liquid product 5 to communicate with the plate 106 and to be also capable of retaining the liquid by the surface tension effect. This arrangement with a spring mechanism 105 makes it possible to compensate the shortening of the applicator element 35 in the course of use. As has been mentioned above, the plate 106 is pierced by one or more slots 103 capable of retaining some of the liquid product 5 by the surface tension effect. In the example shown in FIG. 4, a sectional view of the device of FIG. 3 at the level of the plate 106, the plate 106 has six slots 103 in the form of circular arcs. Alternatively, these slots 103 are disposed radially in the plate 106. Of course, these slots 103 may have any appropriate shape in cross section as, for example, those shapes shown in FIGS. 6/I to 6/V. In longitudinal cross-section these slots 103 may have frustoconical shapes (FIG. 7) or partly frustoconical shapes (FIG. 8) so as to arrange a reserve of the liquid product 5. Typically, such slots 103 have a cross-section comprised between 0.2 and 7 mm$^2$. In an alternative, the elastically deformable element 100 is mounted on a grid, not shown.

The end fitting 11 of this variant is made of a rigid material and has threads 203 on the external surface of its upper portion 202. The upper portion 202 is extended towards the bottom along a flared skirt 200 surrounding the end fitting 11 while being disposed at a radial distance therefrom. The flared skirt 200 surmounts the reservoir 2 of a substantially hemispherical shape, and is joined to the reservoir 2, for example, by bonding or welding. Advantageously, the reservoir 2 is made at least partly of a transparent or translucent material so as to allow the level of the liquid product 5 in the reservoir 2 to be seen. The threads 203 of the end fitting 11 cooperate with threads 403 of the cap 4. In this variant, the applicator element 35 is mounted or attached with force, for example, on an open glove finger 34 which is mounted directly on the neck of the end fitting 11 in a leakproof manner.

Figure 5:
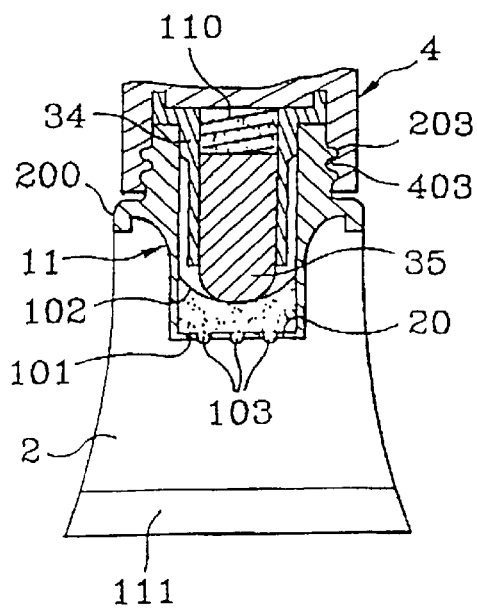
FIG. 5 is a partial sectional view of another variant of the application unit in accordance with the invention.

According to FIG. 5, the application unit is similar to that of FIG. 3, except that the reservoir 2 is a flexible tube joined to the flared skirt 200, here shorter than that of the variant of FIG. 3. The bottom of the tube that is the reservoir 2 is closed at the level of a transverse weld seam 111. Moreover, the shortening of the applicator element 35 in the course of use is compensated for by mounting the applicator element 35 inside the open glove finger 34 by means of a spring 110, whose restoring force pushes back the applicator element 35 in the direction towards the bottom of the reservoir 2. According to this variant, the applicator element 35 can be mounted inside a cup (not shown) joined to the spring 110.

These arrangements with springs 105, 110 illustrated with reference to FIGS. 3 and 5, respectively, are only necessary in the case where the applicator element 35 is subjected to substantial shortening in the course of use. When the shortening is small (less than 5 or 7 mm), the compensation is effected by the elastically deformable element 100 itself, whose thickness and density will be chosen in an adequate manner.

Figure 9:
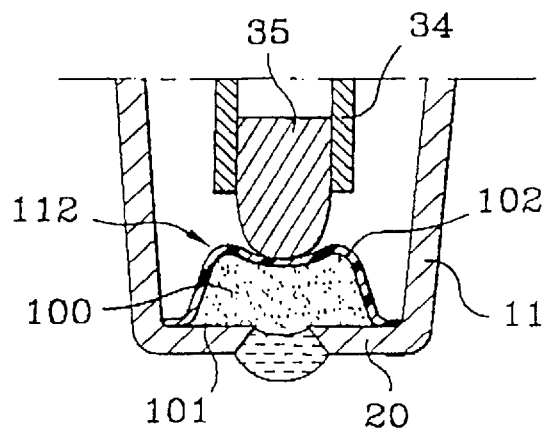
FIG. 9 illustrates a variant of the mounting of the elastically deformable element on the application unit.

FIG. 9 illustrates another variant of mounting the elastically deformable element 100 in the bottom 20 of the end fitting 11. According to this variant, the applicator element 35 is in contact with the elastically deformable element 100 through a porous element 112 of a flexible-to-rigid, or semi-rigid consistency that is perforated or porous. By way of example, a sheet of a thermoplastic elastomer, or a plastic sheet, can be used as the porous element 112. Alternatively, the restoring surface 102 of the elastically deformable element 100 may be covered by a flocked coating, or a layer of felt, or a sheet of a textile material. These arrangements make it possible to substantially modify the restoring bias of the elastically deformable element 100 towards the applicator element 35, as well as the abrasiveness of the elastically deformable element 100.

Figure 10A:
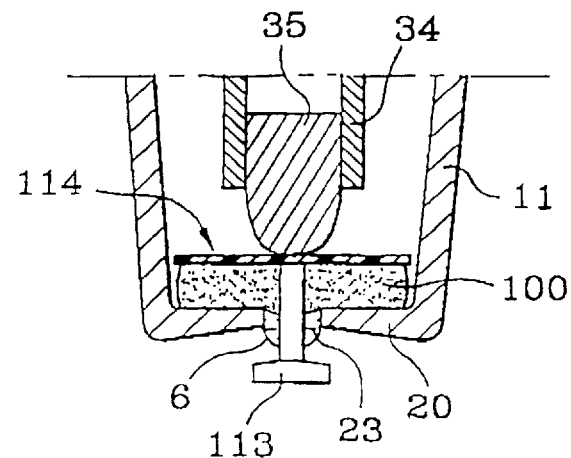
FIGS. 10a and 10b illustrate another variant of the mounting the elastically deformable element on the application unit.
Figure 10B:
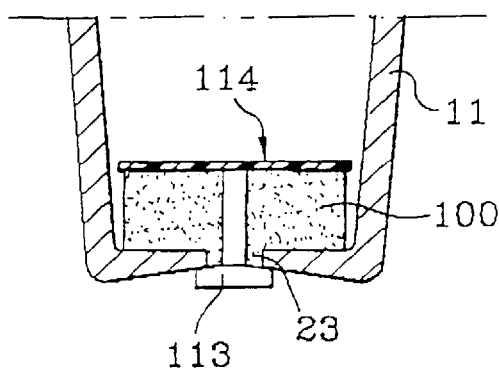

FIGS. 10a and 10b again illustrate a variant of the invention, in which the opening 23 is selectively obturated by means of a valve 113 whose stem traverses the elastically deformable element 100 and is mounted on a perforated plate 114, made for example of an elastomer, whereon the applicator element 35 comes to bear when the cap 4 (not shown) is screwed onto the reservoir 2 (not shown). In this position, illustrated in FIG. 10a, the applicator element 35 bears on the perforated plate 114 causing the valve 113 to be lowered, which un-obturates the opening 23. By shaking the reservoir 2, or by turning it over for instance, a quantity of the liquid 6 can attach itself to the sides of the opening 23. When the applicator element 35 is withdrawn, the valve 113 rises again and obturates the opening 23 in a leakproof manner, the liquid 6 then being absorbed by suction into the elastically deformable element 100 which reassumes its initial volume. This configuration allows the reservoir 2 to be closed in a leakproof manner when the reservoir 2 is not closed by the cap 4, thus avoiding any risk of untimely fouling.

According to an alternative, not shown, the valve 113 is mounted in such a way that it obturates the opening 23 when the applicator element 35 bears on the elastically deformable element 100, and that it releases it when the applicator element 35 is being withdrawn. For this purpose and by way of example, the shutter of the valve 113 is inside the glove finger 11, the bearing of the applicator element 35 on the elastically deformable element 100 causing the shutter to bear on the opening in a leakproof manner. The elasticity of the material forming the foam of the elastically deformable element 100 is sufficient to return the valve 113 into its open position when the applicator element 35 is being withdrawn. Advantageously, the valve 113 is mounted on an auxiliary spring (not shown) allowing the valve 113 to be opened when the applicator element 35 is being withdrawn. This configuration makes it possible to limit the risks of excessive suction of the product forming the applicator element 35, and thus to limit the risks of an in-depth solubilization or gelling of the product forming the applicator element 35. This characteristic is particularly advantageous for certain products forming the applicator element 35 whose process of solubilization or gelling in depth is intensified with the time of contact with the liquid composition and/or with the volume already rendered soluble or gelled.

The invention which has been described above is particularly advantageous, in that it makes it possible to keep the surface of the applicator element in contact with a given liquid composition in a simple and effective way before the application. The adjustment of the quantity of the liquid product delivered to the applicator element can be effected in various ways, either by adjusting the level of pressure of the applicator element on the restoring surface, or by choosing the density and thickness of the elastically deformable element in an appropriate way, or by modifying the restoring surface of the foam of the elastically deformable element by flocking for example, or by interposing between the elastically deformable element and the applicator element a sheet of a material capable of substantially modifying the restoring capacity of the foam. It is, moreover, possible to select the size, number and shape of the openings in contact with the charging surface of the elastically deformable element, so as to limit the absorption of the liquid product by the elastically deformable element.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States:

1. A packaging and application unit having a longitudinal axis, which comprises:
    a reservoir containing a liquid composition;
    an applicator element including a product having a surface which becomes soluble or gels when the surface comes into contact with the liquid composition; and
    an elastically deformable element having a restoring surface and a charging surface opposite the restoring surface, the charging surface being communicable with the liquid composition, wherein a portion of the applicator element is engageable with the restoring surface of the elastically deformable element so as to compress the elastically deformable element from a rest condition into a compressed condition, and wherein the elastically deformable element is charged with the liquid composition by the charging surface upon restoration of the elastically deformable element from the compressed condition to the rest condition.

2. A packaging and application unit according to claim 1, wherein the elastically deformable element is mounted in the reservoir and is made of foam or of an elastomer of low hardness, further comprising a cap detachably mounted on the reservoir, the cap having an applicator holder on which the applicator element is mounted, wherein said applicator element bears on the restoring surface of the elastically deformable element in the closed position of the cap so as to compress said elastically deformable element, and wherein the opening of the cap causes the restoration of the elastically deformable element.

3. A packaging and application unit according to claim 2, further comprising an end fitting mounted in the reservoir, the end fitting having a bottom including retaining means for retaining a quantity of the liquid composition by surface tension, wherein the elastically deformable element is mounted inside the end fitting, the charging surface of the elastically deformable element facing the bottom of the end fitting.

4. A packaging and application unit according to claim 3, wherein the bottom of the end fitting forms a grid.

5. A packaging and application unit according to claim 3, wherein the retaining means includes at least one of an opening and a slot arranged in the bottom of the end fitting.

6. A packaging and application unit according to claim 5, wherein the retaining means includes a plurality of slots forming concentric portions of circular arcs.

7. A packaging and application unit according to claim 6, wherein the retaining means forms a frustoconical flared portion opening out into the reservoir so that the liquid composition in the reservoir may be retained in the flared portion.

8. A packaging and application unit according to claim 5, wherein the retaining means includes a plurality of radial slots.

9. A packaging and application unit according to claim 7, wherein the retaining means forms a frustoconical flared portion opening out into the reservoir so that the liquid composition in the reservoir may be retained in the flared portion.

10. A packaging and application unit according to claim 5, wherein the retaining means forms a frustoconical flared portion opening out into the reservoir so that the liquid composition in the reservoir may be retained in the flared portion.

11. A packaging and application unit according to claim 5, wherein the retaining means forms a central opening, and further comprising a valve for selectively obturating the central opening, wherein the valve opens the central opening by compression of the elastically deformable element, and wherein detachment of the cap from the reservoir and withdrawal of the applicator element produces closing of the central opening by the valve due to expansion of the elastically deformable element.

12. A packaging and application unit according to claim 5, wherein the retaining means forms a central opening, and further comprising a valve for selectively obturating the central opening, wherein the valve closes the central opening by compression of the elastically deformable element, and wherein detachment of the cap from the reservoir and withdrawal of the applicator element produces opening of the central opening by the valve due to expansion of the elastically deformable element.

13. A packaging and application unit according to claim 3, wherein the elastically deformable element is mounted in the bottom of the end fitting by a method selected from the group consisting of bonding, welding, riveting and catch engagement using an annular collar.

14. A packaging and application unit according to claim 2, wherein the applicator element is made of a stick of a solid or semisolid product friable on its surface when the surface contacts the liquid composition, and further comprising a spring mounted between the applicator element and the applicator holder so as to compensate for shortening of the applicator element in the course of use.

15. A packaging and application unit according to claim 2, further comprising a spring mounted between the elastically deformable element and the bottom of the end fitting.

16. A packaging and application unit according to claim 1, wherein the deformable element is made of a foam or an elastomer with open or half-open cells, the restoring surface is covered by a material selected from the group consisting of a flocked coating, a perforated film of a thermoplastic elastomer, a perforated plastic film, a layer of felt, and a layer of a textile material.

17. A packaging and application unit according to claim 1, wherein the reservoir is a tube.

18. A packaging and application unit according to claim 1, wherein the reservoir is made of a translucent material so as to allow the quantity of the liquid composition remaining in the reservoir to be seen.

19. A packaging and application unit according to claim 1, wherein the applicator element is selected from the group consisting of a styptic pencil, a lipstick, a stick of polyvinyl alcohol, a stick of guar gum, and a stick of a product for the treatment of the skin.

20. A packaging and application unit according to claim 1, wherein the liquid composition includes at least one of a water, a solvent, a preservative, an emollient and an active compound.

* * * * *